US009586223B2

(12) United States Patent
Bentvelsen et al.

(10) Patent No.: US 9,586,223 B2
(45) Date of Patent: Mar. 7, 2017

(54) ANALYAIS AND CONTROL OF AEROSOL OUTPUT

(75) Inventors: Peter Henricus Cornelius Bentvelsen, Waalre (NL); Martinue Bernardus Van Der Mark, Best (NL); Hendrik Huijgen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 165 days.

(21) Appl. No.: 14/344,409

(22) PCT Filed: Sep. 10, 2012

(86) PCT No.: PCT/IB2012/054683
§ 371 (c)(1),
(2), (4) Date: Mar. 12, 2014

(87) PCT Pub. No.: WO2013/042002
PCT Pub. Date: Mar. 28, 2013

(65) Prior Publication Data
US 2014/0339323 A1    Nov. 20, 2014

Related U.S. Application Data

(60) Provisional application No. 61/536,107, filed on Sep. 19, 2011.

(51) Int. Cl.
*B05B 12/08* (2006.01)
*A61M 11/00* (2006.01)
(Continued)

(52) U.S. Cl.
CPC ......... *B05B 12/082* (2013.01); *A61M 11/005* (2013.01); *A61M 15/0085* (2013.01);
(Continued)

(58) Field of Classification Search
CPC .............. B05B 12/082; B05B 17/0607; B05B 17/0646; B05B 12/006; A61M 11/005;
(Continued)

(56) References Cited

U.S. PATENT DOCUMENTS 6,158,431 A * 12/2000 Poole ................. A61M 15/0085
128/200.16
7,628,339 B2 * 12/2009 Ivri ..................... B05B 17/0676
128/200.16
(Continued)

FOREIGN PATENT DOCUMENTS

CN    101495168 A    7/2009
JP    5951343 B2    12/1984
(Continued)

*Primary Examiner* — Arthur O Hall
*Assistant Examiner* — Juan C Barrera
(74) *Attorney, Agent, or Firm* — Michael W. Haas

(57) ABSTRACT

An aerosol generation system (and method) comprises an aerosol generating device (1) for generating an aerosol output (2) and controller (12) for controlling the generating device (1) using a generator drive signal. An aerosol density detector (6,9) is used. A time delay measurement device (13) is adapted to derive a timing measurement based on the generator drive signal and the aerosol density detector output, wherein the timing measurement and the aerosol density are combined to derive an aerosol output rate.

14 Claims, 2 Drawing Sheets

(51) Int. Cl.
  *A61M 15/00* (2006.01)
  *G01N 15/06* (2006.01)
  *B05B 17/06* (2006.01)
  *B05B 12/00* (2006.01)
  *G01F 1/74* (2006.01)
  *G01F 1/86* (2006.01)
  *B05B 17/00* (2006.01)
  *G01N 15/00* (2006.01)

(52) U.S. Cl.
  CPC ........ *B05B 12/006* (2013.01); *B05B 17/0607* (2013.01); *G01F 1/74* (2013.01); *G01F 1/86* (2013.01); *G01N 15/06* (2013.01); *A61M 2205/3306* (2013.01); *A61M 2205/3379* (2013.01); *B05B 17/0646* (2013.01); *G01N 2015/0026* (2013.01); *G01N 2015/0693* (2013.01)

(58) Field of Classification Search
  CPC ...... A61M 15/0085; A61M 2205/3306; A61M 2205/3379; G01N 2015/0026; G01N 15/06; G01N 2015/0693; G01F 1/74; G01F 1/86

USPC .............................................. 239/11, 68, 70
  See application file for complete search history.

(56) References Cited

U.S. PATENT DOCUMENTS

| 8,154,711 | B1* | 4/2012 | Scheer ................ B05B 12/082 356/3.01 |
|---|---|---|---|
| 2006/0087651 | A1 | 4/2006 | Montaser et al. |
| 2006/0102178 | A1 | 5/2006 | Feiner et al. |
| 2009/0000391 | A1 | 1/2009 | Dorrmann et al. |
| 2009/0095821 | A1 | 4/2009 | Feriani et al. |
| 2009/0223513 | A1* | 9/2009 | Papania ............ A61M 15/0065 128/200.16 |

FOREIGN PATENT DOCUMENTS

| JP | 2002522755 A | 7/2002 |
|---|---|---|
| JP | 2005049228 A | 5/2005 |
| WO | WO0008419 A1 | 2/2000 |
| WO | WO2006006963 | 1/2006 |
| WO | WO2008016156 | 2/2008 |

* cited by examiner

ANALYAIS AND CONTROL OF AEROSOL OUTPUT

CROSS-REFERENCE TO PRIOR APPLICATIONS

This application is the U.S. National Phase application under 35 U.S.C. §371 of International Application Serial No. PCT/IB2012/054683, filed on Sep. 10, 2012, which claims the benefit of U.S. Application Ser. No. 61/536,107, filed on Sep. 19, 2011. These applications are hereby incorporated by reference herein.

FIELD OF THE INVENTION

This invention relates to the analysis of an aerosol output.

BACKGROUND OF THE INVENTION

Nebulizers generate an aerosol output, and are used for medication delivery through the respiratory channel. The patient receives a specific amount of medication in the form of small droplets (aerosol) that are formed by forcing the medication through a mesh in the form of a thin metal plate with tiny holes.

The volume of medication to be nebulized (typically 0.2 to 2 ml) is dosed into the device, and the device generates the aerosol by means of well known methods such as a vibrating mesh, vibrating horn, or a vibrating flat plate in a resonant cavity. The required ultrasonic vibration is generated by an actuator, typically a piezoelectric crystal. The amount of medication that reaches the patient during the treatment is equal to the supplied medication dose minus the aerosol deposited in the device and residues of medication that remain in the device after the treatment is finished.

For a medication therapy, it is sometimes required that not only the dose is precisely defined, but also the rate at which the medication is delivered, namely the aerosol output rate. The nebulizer generally controls the aerosol output rate by means of the electrical power and driving frequency applied to the piezoelectric drive system.

The aerosol output rate cannot be exactly predicted based on the applied electrical power. Aerosol generating systems may have different efficiencies (amount of aerosol generated per unit electrical power), for example due to device and mesh tolerances, temperature, and cleanliness of the mesh.

A system that estimates the aerosol output rate by measuring the density of the aerosol beam and the air flow rate may be used in a feedback control loop to adjust the electrical power. The aerosol density can be measured by means of an optical beam perpendicular to the aerosol beam. The optical beam can be generated by a light emitting diode (LED). The beam shape of the light from a LED is divergent, and the optical beam may be collimated to a parallel or nearly parallel beam using one or more lenses. The beam may be further shaped using for example a circular or rectangular diaphragm.

The optical beam crosses the aerosol beam, and falls on an optical sensor (optionally through a diaphragm and optionally focused using one or more lenses). The optical system can be calibrated by measuring the sensor signal at a time that no aerosol is present with the LED off ("dark signal") and with the LED on ("light signal"). If the aerosol beam is present, the rays of the optical beam are scattered by the droplets, thus decreasing the light that falls on the optical sensor, and hence decreasing the measured output signal at the optical sensor. The decrease of light on the sensor caused by droplets in the light path is called obscuration. The obscuration can be quantitatively expressed by the parameter ("light signal"-"measured signal")/("light signal"-"dark signal").

The obscuration is a function of the droplet density in the aerosol beam and the length over which the light travels through the aerosol beam. If the velocity of the aerosol beam is known, e.g. through a separate air flow rate measurement (using a differential pressure sensor or a flow sensor), then the aerosol output rate can be computed from the aerosol density and the volume of the aerosol beam that passes the optical beam per unit of time. The volume can be calculated from the product of the cross-sectional area of the aerosol beam and the velocity of the aerosol beam.

The method described above of estimating the aerosol output rate from optical beam obscuration and air flow has the disadvantage that two detection systems are required: the optical system and the air flow measurement system.

The optical system may be located either at a distance from the mesh such that the air flow and droplet velocity are the same, or closer to the surface of the mesh where the droplets are ejected. In this case, the droplet velocity is not strongly related to the air flow but dependent on the nebulizing parameters such as power and frequency of the driver electronics). Both regimes have their own disadvantages.

For an optical system at a distance from the mesh, the aerosol droplets have the same velocity as the surrounding air flow, but aerosol droplets may be deposited on the optical system (e.g. on the lenses) such that the detected signal on the optical sensor decreases. This reduces the reliability of the density measurement, because it is not possible to distinguish if the signal decrease is caused by the aerosol density or the contamination of the optics. This disadvantage may be overcome partially by calibration at regular intervals.

Depending on the mechanical design of the nebulizer, it may be necessary to locate the optical system in the mouthpiece of the nebulizer. Since the mouthpiece is usually a detachable and replaceable part of a nebulizer, the location of the optical system may create design difficulties and increasing costs.

For an optical system close to the mesh, it is possible to construct the optical system in such a way that contamination is to a large extent avoided, but the disadvantage is that the average velocity of the droplets close to the mesh is defined by the aerosol generation system instead of the air flow. Moreover, the average droplet velocity generally increases with higher aerosol output rate. As a result, the density of the aerosol beam (as detected by the optical system) increases only marginally with the aerosol output rate, and cannot be used as reliable estimate of the aerosol output rate.

US 2006/0087651 discloses a system in which the aerosol velocity is obtained by particle image velocimetry, by which particles are mapped through successive images to derive flow vectors for the individual particles. This is a computationally intensive and hardware intensive process.

SUMMARY OF THE INVENTION

According to the invention, there is provided an aerosol generation system, comprising:
an aerosol generating device for generating an aerosol output;
a controller for controlling the aerosol generating device using a generator drive signal;
an aerosol density detector;

time delay measurement means, which is adapted to derive a timing measurement based on the generator drive signal and the aerosol density detector output, wherein the timing measurement and the aerosol density are combined to derive an aerosol output rate.

In this system, aerosol density measurement and droplet velocity are measured with the same system. In particular, no additional physical sensors (such as flow sensors) are required than already provided for aerosol density detection. The time delay measurement is indicative of an average droplet velocity, and the velocity and density together derive the output rate (i.e. the volume or mass of aerosol per unit time). This output rate can then be used as a feedback parameter, for example for controlling a drive power to the aerosol generating device, which can be a piezoelectric drive system.

The aerosol density detector can comprise an optical arrangement. For example, the aerosol density detector can comprise an optical arrangement for measuring optical transmission through the aerosol output. The aerosol density detector can comprise a light source and a light detector disposed on opposite sides of a region through which the aerosol output is directed, and the density is derived from the light detector signal.

The generator drive signal is preferably modulated between on and off states. This enables a timing measurement based on the transition between periods of aerosol generation and periods of no aerosol generation.

For example, the system can be adapted to:

control the aerosol generating device to provide a period of first output level and a period of second output level;
make a timing measurement based on a time delay from the start of the period of first or second output levels to the detection of the resulting change in output by the aerosol density detector;
derive the aerosol velocity from the timing measurement; and
derive the density from the aerosol density detector during a period of output.

One of the first and second output levels can be a no output level, so that the timing is then from the drive signal being applied (off-on) or turned off (on-off) and the detection of the corresponding change in output. The density is then derived from the on period when there is flow. Alternatively, the output levels can both be non-zero, and the change in flow is detected, rather than the start or cease of detected flow.

The invention also provides a method of controlling an aerosol generation system, comprising:

controlling an aerosol generating device with an aerosol generator drive signal;
obtaining a timing measurement based on the generator drive signal and an aerosol density detector output,
combining the timing measurement and a measured aerosol density to derive an aerosol output rate.

The time delay measurement and the aerosol density can be derived repeatedly during aerosol generation and the time delay measurement can be performed less frequently than the aerosol density measurement. For example, the time delay measurement can be derived periodically, with a period of between 2 and 30 seconds and the aerosol density measurement can be derived periodically, with a period of between 0.5 and 2 seconds.

BRIEF DESCRIPTION OF THE FIGURES

Examples of the invention will now be described in detail with reference to the accompanying drawings, in which.

DETAILED DESCRIPTION OF AN EMBODIMENT

The invention provides an aerosol generation system in which a conventional aerosol density detector is used. A time delay measurement device is adapted to derive a timing measurement based on a generator drive signal and the aerosol density detector output. The timing measurement is indicative of a time delay between the aerosol generation and the presence of the generated aerosol at the aerosol density detector, which is at a known distance from the aerosol generator. The timing measurement (which is related to the aerosol velocity) and the aerosol density are combined to derive an aerosol output rate, i.e. the mass transport rate. The aerosol output rate can be used as part of a feedback control mechanism.

Figure 1:
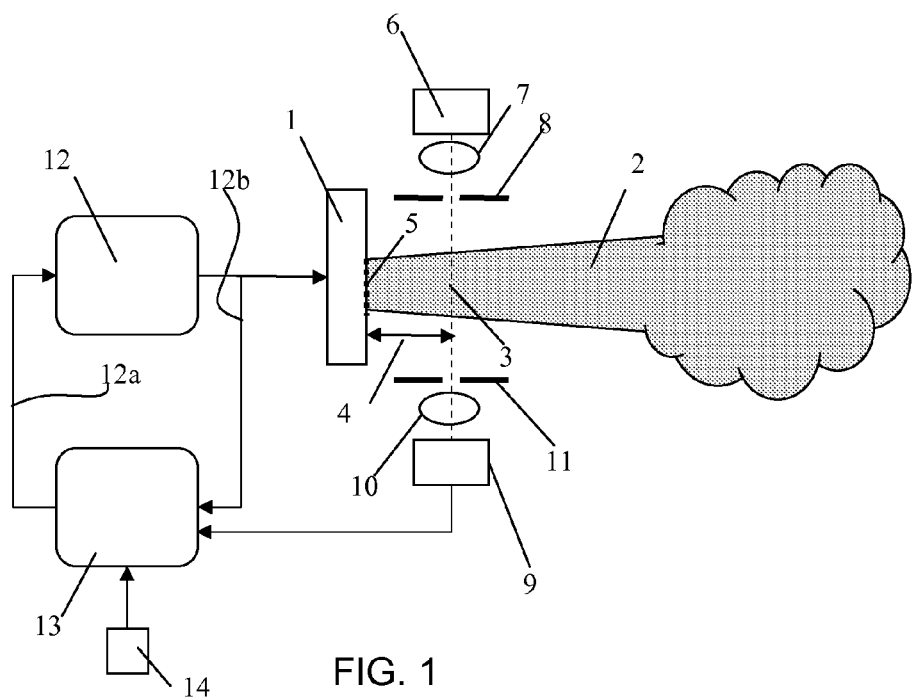
FIG. 1 shows an example of aerosol generation system of the invention.

FIG. 1 shows a nebulizer system of the invention, with a piezoelectric driven aerosol generation system 1 that generates aerosol 2 using a mesh 5. An optical system generates a beam 3 at distance 4 from the mesh 5. The optical system consists of a light source 6 with optional lens 7 and diaphragm 8, and an optical sensor 9 with optional lens 10 and diaphragm 11.

The aerosol generation system 1 is driven by a signal from a drive circuit 12, which thus functions as a controller for controlling the aerosol generation device. The drive signal may be a high frequency signal that is modulated at a lower frequency. The output power may be controlled by either the amplitude of the signal, the duty cycle of the modulation, or both.

The output power of the drive circuit 12 is set by an input signal 12a from a power control feedback system 13 that uses a setting 14 as start value and computes improved settings based on the output 12b of the drive circuit 12 and the output of the optical sensor 9. This system is implemented as an algorithm running on a microcontroller.

The air flow can for example be generated by inhaling. The air flow is detected with a flow sensor (not shown), which starts an algorithm that switches on/off the drive signal to the generator; which in turn starts producing the aerosol.

In alternative embodiments, there may be other means to start the aerosol generation, for example a ventilator/fan that is operated by a start/stop button.

The amount of administered medicine is only dependent on the aerosol generator output, and is not influenced by the air flow. The velocity of the droplets is initially determined by the aerosol generator, and as they are taken into the air flow, the droplets will accommodate to the speed of the air.

Figure 2:
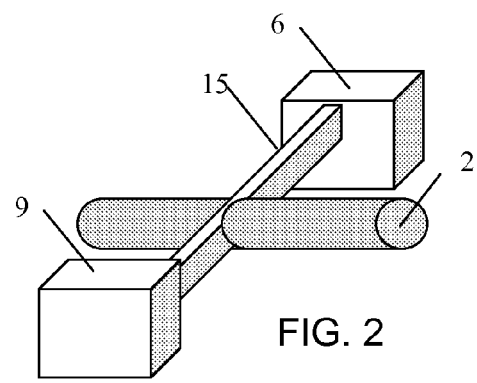
FIG. 2 shows how the aerosol output interacts with the light detection system.

FIG. 2 shows an example of the optical beam. A light beam 15 is emitted from the light source 6 (which can include the lens and diaphragm). The height of the optical beam is such that preferably (but not necessarily) the entire aerosol beam 2 is captured. The width of the optical beam is preferably small (typically 0.5 to 2 mm), to achieve sufficient time resolution for the droplet velocity measurements as explained below. The optical beam falls on the optical sensor 9, again typically with a lens and diaphragm.

The optical system is used both for density measurement in known manner, by measuring the degree of obscuration of the light beam by the aerosol particles, but also for velocity measurement.

Figure 3:
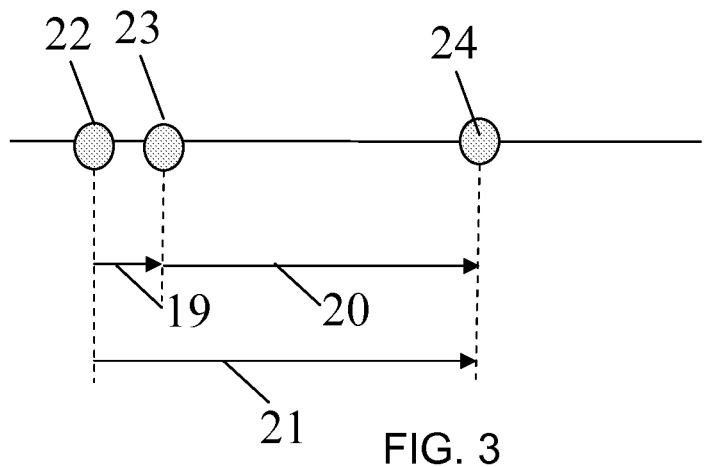
FIG. 3 shows how timing measurements are used.

FIG. 3 shows a timing diagram to explain the velocity measurement.

After the start 22 of the piezoelectric drive signal, there is an unknown time delay $t_G$ (19) until the time 23 at which droplets are generated at the mesh surface. The droplets leave the mesh and arrive at time 24, which is after travel time $t_T$ (shown as 20), at the centre of the optical beam. The optical beam is at a fixed distance D (shown as 4 in FIG. 1).

The velocity $v=D/t_T$ of the droplets can be estimated from the measured time $t_M$ (shown as 21) from the start of the piezoelectric drive signal to the detection of the droplets at the optical sensor, assuming that $t_G$ (shown as 19) is negligible.

Figure 4:
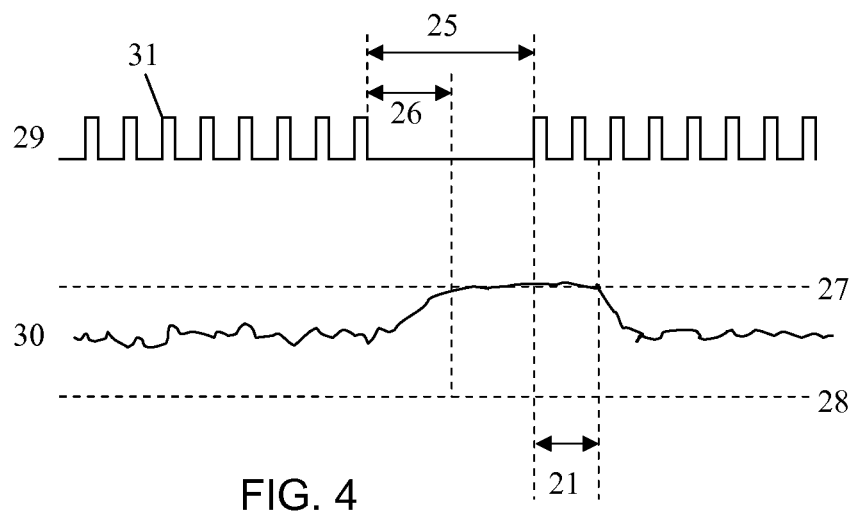
FIG. 4 is used to explain the timing measurements in more detail.

As shown in FIG. 4, the piezoelectric drive signal 29 consists of a series of short bursts 31 of high frequency waves. The optical signal 30 received by the sensor can vary between a light signal 27 (where there is no obscuration) and a dark signal 28 (where there is total obscuration). The signal level thus depends on the aerosol density. As shown in FIG. 4, the aerosol density in practice never results in a dark signal, but results in an intermediate signal level.

For the purposes of the velocity measurement, the piezoelectric drive signal is paused for a duration 25, typically 50 to 1000 ms. After a shorter duration 26, the optical signal is at the "light signal" level because there is no more aerosol obscuration of the optical beam.

On resuming the drive signal at the end of the pause, the duration $t_M$ (shown as 21) is measured between the start of the first burst and the time at which the optical signal starts to drop because of obscuration by the first aerosol droplets arriving at the optical beam.

This duration is proportional to the velocity under the condition that $t_G$ is negligible.

To make $t_G$ negligible, the distance D of the optical sensor from the mesh is chosen such that the time of flight $t_M$ is much larger than the time delay $t_G$ between the actuation of the drive system and the generation of aerosol droplets at the mesh.

A typical example of the distance D is 5.5 mm (in the range 1 mm to 15 mm). In one example, the measured time $t_M$ was measured to be of the order of 1.5 ms corresponding to an average velocity of flow over the 5.5 mm distance of 3.7 m/s (if $t_G$ is neglected). The ejection speed is higher, and this speed drops off towards the air flow speed. For example, the ejection speed very close to the mesh may be in the range 10 m/s to 30 m/s. The air flow is typically in the range 5 to 80 l/min, and in one example, output tube has a 22 mm diameter. A typical lower limit for the air flow speed is around 1 m/s, so that the average velocity will be approximately in the range 1 m/s (a typical lowest air flow speed) to 30 m/s (a typical maximum droplet ejection speed). In one example of device, the aerosol output rate can be in the range 200 mg/min to 1500 mg/min.

These ranges are not intended to be limiting, but are provided to give a feeling for the scale of the various parameters.

The time delay $t_G$ is neglected in the calculations above. $t_G$ has been measured by separate experiment, and found to be typically in the range 10 to 50 µs, which is indeed negligible compared to the timing measurement.

The aerosol density and velocity can be used as feedback control parameters (in known manner) to control the aerosol delivery.

Figure 5:
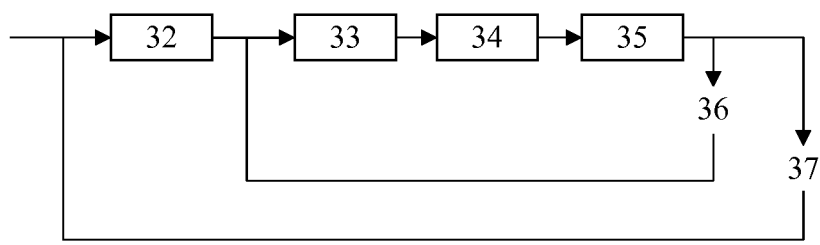
FIG. 5 shows the method of the invention.

FIG. 5 shows a flow chart of the method of the invention for aerosol output rate control during aerosol delivery.

The droplet velocity is measured in step 32 according to the method described above, and the aerosol density is measured in step 33.

These values are used to calculate the output rate in step 34. The piezoelectric drive power is adjusted accordingly in step 35.

The sequence 33, 34, 35, which performs the density measurement, is repeated in a loop 36 a number of times at a typical cycle time of 0.5 to 2 seconds, while the velocity measurement is repeated in a loop 37 at a slower pace, to avoid frequent interruptions of the aerosol beam. The cycle time of the velocity measurements is typically 2 to 30 seconds.

The invention can be applied to a jet nebulizer (which has the air flow generated by a compressor), or a pressurized metered dose inhaler (pMDI). The invention is of particular interest for ultrasonic nebulizers as outlined above, particularly using Vibrating Mesh Technology (VMT).

The invention can in fact be applied to the analysis and control of any aerosol. A nebulizer is only one example of device which uses an aerosol output which needs to be controlled. Other examples are air humidifiers and paint spraying equipment. The invention is of interest when there is a need for accurate dosing measurement, while at the same time there is no possibility to measure the output rate on the supply channel to the aerosol generator (e.g. by placing the supply container on a scale).

The invention can use a known optical sensor arrangement, and for this reason, the optics have not been described in detail. The invention can be implemented as only a modified control approach for controlling the generation of the aerosol, and a timing system for measuring the time delay.

Similarly, the aerosol generation system can be completely conventional, and can be of various different types, and thus has not been described in detail.

In the example above, the optical detection of aerosol density is based on a measurement of the obscuration of a signal passing through the aerosol output. However, optical density can also be measured based on reflected or scattered light from the aerosol output, which also depend on the aerosol density. Aerosol density measurements may also be performed by non-optical means, for example the distortion or attenuation of ultrasound through the aerosol beam, or with radio frequency analysis.

In the example above, the time delay measurement is based on a period of no output and a period of output. This provides a clean interface between signals being detected. However, the time delay measurement may be based on a change in detected non-zero levels. Different non-zero levels can be created using the pulse width modulation (PWM) drive scheme, rather than requiring an additional off period to be defined. Thus, the example above shows the interruption of the PWM drive signal, but the actual PWM pulses can instead be used for the timing information.

Modulation of the control bursts provides a modulation of the average power which affects the aerosol output rate. This can be based on modulation of width of the bursts or the amplitude, or the repetition rate.

Thus, in general terms, the invention uses knowledge of the drive signal to the aerosol generator, in combination with detection of the resulting aerosol pattern downstream of the aerosol generator, to derive a time signal and therefore an average velocity indication.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. An aerosol generation system, comprising:
an aerosol generating device for generating an aerosol output;
a controller for controlling the aerosol generating device using a generator drive signal;
an aerosol density detector that measures aerosol density; and
time delay measurement means, which is adapted to derive a timing measurement based on the generator drive signal and the measured aerosol density, wherein the controller is arranged to combine the timing measurement and the measured aerosol density to derive an aerosol output rate, and wherein the timing measurement and the measured aerosol density are derived repeatedly during aerosol generation, and the timing measurement is performed less frequently than the measurement of the aerosol density.

2. A system as claimed in claim 1, wherein the aerosol density detector comprises an optical arrangement.

3. A system as claimed in claim 2, wherein the aerosol density detector comprises an optical arrangement for measuring optical transmission through the aerosol output.

4. A system as claimed in claim 3, wherein the aerosol density detector comprises a light source and a light detector disposed on opposite sides of a region through which the aerosol output is directed, wherein the density is derived from the light detector signal.

5. A system as claimed in claim 1, wherein the generator drive signal is modulated between on and off states.

6. A system as claimed in claim 1, adapted to:
control the aerosol generating device provide a period of first output level and a period of second output level;
make a timing measurement based on a time delay from the start of the period of first or second output level to the detection of the resulting change in output by the aerosol density detector;
derive aerosol velocity from the timing measurement; and
derive the density from the aerosol density detector during a period of output.

7. A system as claimed in claim 1, wherein the controller is adapted to control the aerosol generating device by controlling a drive power to the aerosol generating device in dependence on the derived aerosol output rate.

8. A system as claimed in claim 1, wherein the aerosol generating device comprises a piezoelectric drive system.

9. A method of controlling an aerosol generation system, comprising:
controlling an aerosol generating device with an aerosol generator drive signal;
measuring aerosol density with an aerosol density detector:
obtaining a timing measurement based on the generator drive signal and the measured aerosol density,
combining the timing measurement and the measured aerosol density to derive an aerosol output rate, wherein the timing measurement and the measured aerosol density are derived repeatedly during aerosol generation, and the timing measurement is performed less frequently than the measurement of the aerosol density.

10. A method as claimed in claim 9, comprising:
controlling the aerosol generating device to provide a period of first output level and a period of second output level;
obtaining the timing measurement from the start of the period of first or second output levels to the detection of a resulting change in output within the aerosol density detector output;
the aerosol density during a period of output; and
deriving the aerosol output rate from the timing measurement and the aerosol density.

11. A method as claimed in claim 9, comprising controlling the aerosol generating device by controlling a drive power to the aerosol generating device using the drive signal, the drive signal modulated between on and off states, such that when the drive signal is in the off state there is no output from the aerosol generating device.

12. A method as claimed in claim 11, wherein the period of no output has a duration of between 50 ms and 1 second.

13. A method as claimed in claim 9, wherein the timing measurement is derived periodically, with a period of between 2 and 30 seconds and the aerosol density measurement is derived periodically, with a period of between 0.5 and 2 seconds.

14. A method as claimed in claim 9, comprising controlling the aerosol generating device controlling a drive power to the aerosol generating device in dependence on the derived aerosol output rate.

* * * * *